US 7,101,685 B2

(12) United States Patent
Nagai et al.

(10) Patent No.: US 7,101,685 B2
(45) Date of Patent: *Sep. 5, 2006

(54) RECOMBINANT SENDAI VIRUS

(75) Inventors: Yoshiyuki Nagai, Tokyo (JP); Atsushi Kato, Tokyo (JP); Fukashi Murai, Ibaraki (JP); Tsuneaki Sakata, Osaka (JP); Mamoru Hasegawa, Ibaraki (JP); Tatsuo Shioda, Tokyo (JP)

(73) Assignee: DNAVEC Research Inc., Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/728,207

(22) Filed: Dec. 1, 2000

(65) Prior Publication Data

US 2002/0098576 A1 Jul. 25, 2002

Related U.S. Application Data

(63) Continuation of application No. 09/071,591, filed on May 1, 1998, now abandoned, which is a continuation of application No. PCT/JP96/03069, filed on Oct. 22, 1996.

(30) Foreign Application Priority Data

Nov. 1, 1995 (JP) .............................................. 7-285417

(51) Int. Cl.
C12N 15/09 (2006.01)
A61K 39/155 (2006.01)

(52) U.S. Cl. ................. 435/69.1; 435/235.1; 435/320.1; 435/325; 424/211.1; 536/23.72

(58) Field of Classification Search .............. 435/235.1, 435/320.1, 325, 69.1, 975, 471, 472; 536/27.3, 536/23.72; 424/211.1
See application file for complete search history.

(56) References Cited

U.S. PATENT DOCUMENTS

| 5,166,057 | A |   | 11/1992 | Palese et al. |   |
|---|---|---|---|---|---|
| 5,217,879 | A | * | 6/1993 | Huang et al. ............... | 435/69.1 |
| 5,445,953 | A | * | 8/1995 | Dorner et al. ............ | 435/320.1 |
| 5,578,473 | A | * | 11/1996 | Palese et al. ............ | 435/320.1 |
| 5,665,362 | A | * | 9/1997 | Inglis et al. ............. | 424/205.1 |
| 5,716,821 | A |   | 2/1998 | Wertz et al. |   |
| 5,780,280 | A | * | 7/1998 | Lebkowski et al. ....... | 435/320.1 |
| 6,033,886 | A |   | 3/2000 | Conzelmann |   |
| 6,231,868 | B1 | * | 5/2001 | Vakharia et al. .......... | 424/204.1 |
| 6,514,728 | B1 | * | 2/2003 | Kai et al. ................... | 435/69.5 |
| 6,645,760 | B1 | * | 11/2003 | Nagai et al. ................ | 435/325 |
| 6,723,532 | B1 | * | 4/2004 | Nagai et al. ............... | 435/69.1 |
| 6,746,860 | B1 | * | 6/2004 | Tokusumi et al. ....... | 435/235.1 |

FOREIGN PATENT DOCUMENTS

| EP | 0 440 219 | 8/1991 |
|---|---|---|
| EP | 08/64645 | 9/1998 |
| EP | 0864645 A1 | 9/1998 |
| JP | 4-30791 | 2/1992 |
| JP | 5-85943 | 4/1993 |
| JP | 5-301895 | 11/1993 |
| WO | WO94/08022 | 4/1994 |
| WO | WO 96/10400 | 4/1996 |
| WO | WO97/06270 | 2/1997 |
| WO | WO 97/41245 | 11/1997 |
| WO | WO04/038029 | 5/2004 |

OTHER PUBLICATIONS

Park et al (Proc. Natl. Acad. Sci. USA 88:5537–5541, 1991).*
Hsu et al (Virology 146:38–49, 1985).*
Ogura et al (Journal of General Virology 55:469–473, 1981).*
Middleton et al (Virology 176:656–657, 1990).*
Gotoh et al (Virology 171:434–443, 1989).*
M. Hamaguchi et al.,"Transcriptive Complex of Newcastle Disease Virus," Virology 128: 105–117, 1983.
B. Gotoh et al.,"An endoprotease homologous to the blood clotting factor X as a determinant of viral tropism in chick embryo," EMBO J. 9: 4189–4195, 1990.
T. Shioda et al.,"Determination of the complete nucleotide sequence of the Sendai virus genome RNA and the predicted amino acid sequences of the F, HN and L proteins," Nucleic Acids Res. 14: 1545–1563, 1986.
H. Kido et al.,"Molecular basis of proteolytic activation of Sendai virus infection and the defensive compounds for infection," Biol. Chem. 378: 255–263,1997.
J. K. Ghosh et al.,"A leucine zipper motif in the ectodomain of Sendai virus fusion protein assembles in solution and in membranes and specifically binds biologically–active peptides and the virus," Biochemistry 36: 15451–15462, 1997.
A. Kato et al.,"Initiation of Sendai virus multiplication from transfected cDNA or RNA with negative or positive sense," Genes to Cells 1: 569–579, 1996.
A. Kato et al.,"The paramyxovirus, Sendai virus, V protein encodes a luxury function required for viral pathogenesis," EMBO J. 16: 578–587, 1997.
A. Kato et al., "Importance of the cysteine–rich carboxyl–terminal half of V protein for Sendai virus pathogenesis," J. Virol. 71: 7266–7272, 1997.
M. Tashiro et al.,"Involvement of the mutated M protein in altered budding polarity of a pantropic mutant, F1–R, of Sendai virus," J. Virol. 70: 5990–5997, 1996.

(Continued)

*Primary Examiner*—James Housel
*Assistant Examiner*—Stacy B. Chen
(74) *Attorney, Agent, or Firm*—Chalin A. Smith; Smith Patent Consulting (57) ABSTRACT

A method for generating Sendai virus particles by transfecting the Sendai virus genome to a host expressing all genes for the initial viral replication has been developed, enabling the genetic manipulation of Sendai virus and effective utilization of said virus as the vector.

17 Claims, 3 Drawing Sheets

OTHER PUBLICATIONS

J. Curran et al.,"The Sendai virus P gene expresses both an essential protein and an inhibitior of RNA synthesis by shuffling modules via mRNA editing," EMBO J. 10: 3079–3085, 1991.

J. Curran et al.,"The hypervariable C–terminal tail of the Sendai paramyxovirus nucleocapsid protein is required for template function but not for RNA Encapsidation," J. Virol 67: 4358–4364, 1993.

D. Garcin at al.,"A highly recombinogenic system for the recovery of infectious Sendai paramyxovirus from cDNA: generation of a novel copy–back nondefective interfering virus," EMBO J. 14: 6087–6094, 1995.

C. Delenda et al.,"Normal cellular replication of Sendai virus without the trans–frame, nonstructural V protein," Virology 228: 55–62, 1997.

D. Garcin et al.,"A point mutation in the Sendai virus accessory C proteins attenuates virulence for mice, but not virus growth in cell culture," Virology 238: 424–431, 1997.

C. Tapparel et al.,"Inhibition of Sendai virus genome replication due to promoter–increased selectivity: a possible role for the accessory C proteins," J. Virol. 71: 9588–9599, 1997.

K. H. Park et al.,"Rescue of a foreign gene by Sendai virus," Proc. Natl. Acad. Sci. USA 88: 5537–5541, 1991.

K. H. Park et al.,"In vivo model for pseudo–templated transcription in Sendai virus," J. Virol. 66: 7033–7039, 1992.

P. Calain et al.,"The rule of six, a basic feature for efficient replication of Sendai virus defective interfering RNA," J. Virol 67: 4822–4830, 1993.

P. Calain et al.,"Molecular cloning of natural paramyxovirus copy–back defective interfering RNAs and their expression from DNA," Virology 191: 62–71,1992.

P. Calain et al.,"Functional characterisation of the genomic and antigenomic promoters of Sendai virus" Virology 212: 163–173, 1995.

G. Mottet et al.,"A Sendai virus vector leading to the efficient expression of mutant M proteins interfering with virus particle budding" Virology 221: 159–171, 1996.

F. Radecke et al.,"The nonstructural C protein is not essential for multiplication of edmonston B strain measles virus in cultured cells" Virology 217: 418–421, 1996.

V.M. Hill et al.,"A minor microtubule–associated protein is responsible for the stimulation of vesicular stomatitis virus transcription in vitro" J. General Virology 71: 289–298, 1990.

K. Mizumoto et al.,"Protein factors required for in vitro transcription of Sendai virus genome" J. Biochem. 117: 527–534, 1995.

T. Takagi et al.,"In vitro mRNA synthesis by Sendai virus: isolation and characterization of the transcription initiation complex" J. Biochem. 118: 390–396, 1995.

S. A. Moyer et al.,"Tubulin: A factor necessary for the synthesis of both Sendai virus and vesicular stomatitis virus RNAs" Proc. Natl. Acad. Sci. USA 83: 5405–5409, 1986.

R. Chandrika et al.,"Mutations in conserved domain I of the Sendai virus L polymerase protein uncouple transcription and replication" Virology 213: 352–363, 1995.

S. M. Horikami et al.,"The Sendai virus C protein binds the L polymerase protein to inhibit viral RNA synthesis" Virology 235: 261–270, 1997.

W. J. Neubert et al.,"Transient rescue of Sendai–6/94 ci virus from the persistently infected cell line Ci–E–8 by cocultivation" Virology 125: 445–453, 1983.

M. Sigmund et al.,"Simple method for rapid and highly sensitive detection of antiviral–antibodies in serum and cerebrospinal fluid of small laboratory animals" Journal of Virological Methods 22: 231–238, 1988.

H. Einberger et al.,"Purification, renaturation, and reconstituted protein kinase activity of the Sendai virus large (L) protein: L protein phosphorylates the NP and P proteins in vitro" J. Virol. 64: 4274–4280, 1990.

H. E. Homann et al.,"Sendai virus gene expression in lytically and persistently infected cells" Virology 177: 131–140, 1990.

H. E. Homann et al.,"Sendai Virus protein–protein interactions studied by a protein–blotting protein–overlay technique: mapping of domains on NP protein required for binding to P protein" J. Virol. 65: 1304–1309, 1991.

W. Willenbrink et al.,"Long–term replication of Sendai virus defective interfering particle nucleocapsids in stable helper cell lines" J. Virol. 68: 8413–8417, 1994.

C. J. Buchholz et al.,"The conserved N–terminal region of Sendai virus nucleocapsid protein NP is required for nucleocapsid assembly" J. Virol. 67: 5803–5812, 1993.

P. L.. Collins et al.,"Rescue of synthetic analogs of respiratory syncytial virus genomic RNA and effect of truncations and mutations on the expression of a foreign reporter gene" Proc. Natl. Acad. Sci. USA 88: 9663–9667, 1991.

P. L.. Collins et al.,"production of infectious human repiratory syncytial virus from cloned cDNA confirms an essential role for the transcription elongation factor form the 5' proximal open reading frame capability for vaccine delelomment" Proc. Natl. Acad. Sci. USA 92: 11563–11567, 1995.

A. P Durbin et al.,"Recovery of infection human parainfluenza type 3 from cDNA" Virology 235: 323–332, 1997.

A. P. Durbin et al.,"Minimum protein requirements for transcription and RNA replicationof a minigenome of human parainfluenza virus type 3 and evaluation of the rule of six" Virology 234: 74–83, 1997.

A. Bukreyev et al.,"Recombinant respiratory syncytial virus from which the entire SH gene has been deleted grows efficiently in cell culture and exhibits site–specific attenuation in the respiratory tract of the mouse" J. Virol. 71: 8973–8982, 1997.

K.–K. Conzelmann et al.,"Genetic engineering of animal RNA viruses" Trends in Microbiology 4: 386–393 1996.

M. J. Schnell et al.,"Infections rabies viruses from cloned cDNA" EMBO J. 13: 4195–4203, 1994.

K. Tanabayashi et al.,"Functional interaction of paramyxovirus glycoproteins: Identification of a domain in sendai virus NH which promotes cell fusion" J. Virol. 70: 6112–6118, 1996.

L. S. Tsimring et al.,"RNA virus evolution via a fitness–space model" Physical Review Letters 76: 4440–4443, 1996.

E. Domingo et al.,"Basic concepts in RNA virus evolution" FASEB J. 10, 859–864, 1996.

P. Palese,"Genetic engineering of infectious negative–strand RNA viruses" Trends in Microbiology 3: 123–125, 1995.

P. Palese et al.,"Negative–strand RNA viruses: Genetic engineering and applications" Proc. Natl. Acad. Sci. USA 93: 11354–11358, 1996.

T. Sakaguchi et al.,"Expression of the HN, F, NP and M proteins of Sendai virus by recombinant vaccinia viruses and their contribution to protective immunity against sendai virus infections in mice" J. General Virology 74: 479–484, 1993.

J. L. Hurwitz et al.,"Intranasal sendai virus vaccine protects African green monkeys from infection with human parainfluenza virus–type one" Vaccine 15: 533–540, 1997.

C. J. Buchholz et al.,"The carboxy–terminal domain of sendai virus nucleocapsid protein is involved in complex formation between phosphoprotein and nucleocapsid–like partickes" Virology 204: 770–776, 1994.

K. C. Gupta et al.,"Lack of correlation between sendai virus P/C mRNA structure and its utilization of two AUG start sites from alternate reading frames: Implications for viral bicistronic mRNAS" Biochemistry 35: 1223–1231, 1996.

B.P. De et al.,"Rescue of synthetic analogs of genome RNA of human parainfluenza virus type3" Virology 196: 344–348, 1993.

P. Latorre et al.,"The various sendai virus C proteins are not functionally equivalent and exert both positive and negative effects on viral RNA accumulation during the course of infection" J. Virol. 72: 5984–5993, 1998.

K.–K. Conzelmann,"Genetic manipulation of non–segmented negative–strand RNA viruses" J. General Virology 77: 381–389, 1996.

B. P. De et al.,"Reverse genetics of negative strand RNA viruses" Indian Journal of Biochemistry & Biophysics 31: 367–376, 1994.

T. Tao et al.,"Host range restriction of parainfluenza virus growth occurs at the level of virus genome replication" Virology 220: 69–77, 1996.

D. S. Lyles et al.,"Complementation of M gene mutants of vesicular stomatitis virus plasmid–derived M protein converts spherical extracellular particles into native bullets shapes" Virology 217: 76–87, 1996.

A. Bridgen et al.,"Rescue of a segmented negative–strand RNA virus entirely from cloned complementary DNAs" Proc. Natl. Acad. Sci. USA 93: 15400–15404, 1996.

M. M. Rolls et al.,"Expression of additional genes in a vector derived from a minimal RNA virus" Virology 218: 406–411, 1996.

H. Kido et al.,"Molecular basis of proteolytic activation of Sendai virus infection and defensive compounds for infection" Biol. Chem. 378: 255–263, 1997.

Nakanishi et al., "Sendai Virus as a Candidate of a New Type of Viral Vector", J. Cell. Biochem Suppl. 21A, p. (6–33), 1995.

Tuffereau et al., Direct Adverse Effects of Sendai Virus Dl Particles on Virus Budding and on M Protein Fate and Stability, Virology 162, 417–426, 1988.

Kondo et al., "Temperature–sensitive Phenotype of a Mutant Sendai Virus Strain is Caused by its Insufficient Accumulation of the M Protein", The Journal of Biological Chemistry, vol. 268. No. 29, 21924–21930, 1993.

Stricker et al., "The Sendai Virus Matrix Protein Appears to be Recruited in the Cytoplasm by the Viral Nucleocapsid to Function in Viral Assembly and Budding", Journal of General Virology, 75, 1031–1042, 1994.

Gotoh et al., "Rescue of Sendai Virus from Viral Ribonucleoprotein–Transfected Cells by Infection with Recombinant Vaccinia Viruses Carrying Sendai Virus L and P/C Genes", Virology 171, 434–443, 1989.

Cameron, E. Mol. Biotech. 7:253–265 (1997).

Conzelmann, KK et al. J. Virol. 68(2): 713–719 (1994).

Garcia–Sastre, A. et al., Ann. Rev. Microbiol. 47:765–90 (1993).

Hammer, R. et al., Cell 63:1099–1112 (1990).

Hasan, M. et al., J. Gen. Virol. 78:2813–2820 (1997).

Luytjes, W. et al., Cell 59:1107–1113 (1989).

Malinoski, F. et al., Virology 110:281–291(1981).

Metsikko, K. et al., J. Virology 63(12): 5111–5118 (1989).

Mullins, J. Hypertension 22(4):630–633 (1993).

Peavy, D. et al., J. Immunol. 126(3): 861–864 (1981).

Pekosz, A. et al., PNAS USA 96:8804–8806 (Aug., 1999).

Sakai, Y. FEBS Letters 456:221–226 (1999).

Schnell, J. EMBO Journal 13(18):4195–4203 (1994).

Seidel, G.E., J. Anim. Sci. 71 Suppl 3: 26–33 (1993).

Toriyoshi, H. et al., Aids Res. & Human Retroviruses 15(12): 1109–1120.

Tokusumi, T. et al., Virus Research 86: 33–38 (2002).

Yonemitsu, Y. et al., Surgery 131(1): S261–268 (Jan., 2002).

Hahn, CS et al., Proc Natl Acad Sci USA, vol. 89(7):2679–83 (1992).

Lawson, ND, et al., Proc Natl Acad Sci USA, vol. 92(18):8388–92 (1995).

Whelan, SP et al., Proc Natl Acad Sci USA, vol. 89(7):4477–81 (1995).

U.S. Appl. No. 10/532,172, filed Apr. 4, 2005, Okano et al.

* cited by examiner

RECOMBINANT SENDAI VIRUS

The present application is a Continuation of U.S. Application Ser. No. 09/071,591, filed May 1, 1998, now abandoned, which is a Continuation of PCT/JP96/03069, filed Oct. 22, 1996, which claims priority to Japanese Application No. JP 7-285417, filed Nov. 1, 1995.

FIELD OF THE INVENTION

The present invention relates to the recombinant Sendai virus and the method for preparing the same.

BACKGROUND OF THE INVENTION

Sendai virus is also named hemagglutinating virus of Japan (HVJ), and classified in parainfluenza virus type I, belonging to the genus Paramyxovirus of the family Paramyxoviridae.

Sendai virus particle is pleomorphic, having the genome RNA without a function as template for translation (hereafter designated "negative strand RNA") enclosed in an envelope of 150–200 nm in diameter. Historically, Sendai virus has also been regarded as an industrially useful virus, being widely utilized, especially for the production of heterokaryons and hybrid cells, by taking advantage of viral cell-fusion capacity. Also, cell-fusing liposomes have been developed as a vehicle for gene therapy. Furthermore, Sendai virus is also used as the inducer for various interferons.

According to the classification based on the karyotype of genome nucleic acid, Sendai virus belongs to a group of negative single-strand RNA viruses of negative strand RNA viruses among RNA viruses. RNA viruses are classified into three groups, the dsRNA viruses (double stranded RNA viruses), positive strand RNA viruses, and negative strand RNA viruses. The ds RNA virus group includes reovirus, rotavirus, phytoreovirus, etc., and have segmented, plural filamentous dsRNA genome. Positive strand RNA viruses include poliovirus, Sindbis virus, Semliki forest virus, and Japanese B encephalitis virus, which possess a single positive sense RNA as genome. The genome RNA can function as an mRNA and is capable of producing proteins required for RNA replication and particle formation depending on the translational functions of host cells. In other words, the genome RNA itself of positive strand RNA viruses is capable of disseminating. In the present specification, by "disseminative capability" is meant "the capability to form infectious particles or their equivalent complexes and successively disseminate them to other cells following the transfer of nucleic acid into host cells by infection or artificial techniques and the intracellular replication of said nucleic acid. Sindbis virus classified to positive strand RNA viruses and Sendai virus classified to negative strand RNA viruses have both infectivity and disseminative capability. On the other hand, adeno-associated virus classified to the parvovirus family has the infectivity but no disseminative capability (the mixed infection of adenovirus is necessary for the formation of viral particles). Furthermore, the positive strand RNA derived from Sindbis virus which is artificially transcribed in vitro is disseminative (to form infectious viral particles when transfected into cells). In contrast, not only negative strand but also positive strand of Sendai viral RNA artificially transcribed in vitro is not disseminative (form no infectious viral particles when transfected into cells).

Recently, viral vectors have been used as vehicles for gene therapy. In order to use them as gene therapy vectors, it is necessary to establish techniques for reconstituting viral particles. (By "reconstitution of viral particles" is meant the artificial formation of viral genome nucleic acid and the production of original or recombinant viruses in vitro or intracellularly.) This is because, in order to transfer foreign genes into viral vectors, viral particles should be reconstituted from the viral genome with foreign genes integrated by the gene manipulation. Once techniques of viral reconstitution are established, it becomes possible to produce viruses with a desired foreign gene introduced, or with desired genes deleted or inactivated.

Also, once the viral reconstitution system is constructed and the viral gene manipulation becomes possible, said system appears to become a potential tool for genetically analyzing the viral function. Genetic analysis of viral functions is very important from the medical viewpoint of prevention and therapy of diseases etc. For example, if the replication mechanism of viral nucleic acid is elucidated by utilizing the differences between viral metabolism and host-cellular metabolism, it may be possible to develop viricide acting on the viral nucleic replication process and less damaging to host cells. Also, by elucidating functions of viral gene-encoded proteins, it may become possible to develop antiviral drugs targeting proteins related with the viral infectivity and particle formation. Furthermore, by modifying genes concerned with the membrane fusion and preparing liposomes with superior membrane-fusing capability, it will be able to use them as gene therapy vectors. In addition, as represented by the interferon, the viral infection may induce the activation of host genes for viral resistance, resulting in the enhanced viral resistance of hosts. Genetic analysis of virus functions may provide more important information on the activation of host genes.

Reconstitution of DNA viruses possessing DNA as the genomic nucleic acid has been performed for some time, and can be carried out by the introduction of the purified genome itself, such as SV40, into monkey cells [J. Exp. Cell Res., 43, 415–425 (1983)].

Reconstitution of RNA viruses containing an RNA genome has been preceded by positive strand RNA viruses since genomic RNAs also function as mRNA. For example, in the case of poliovirus, the disseminative capability of the purified genomic RNA itself was already demonstrated in 1959 [Journal of Experimental Medicine, 110, 65–89 (1959)]. Then, it was achieved to reconstitute Semliki forest virus (SFV) by the introduction of cloned cDNAs into host cells utilizing DNA-dependent RNA polymerase activity of host cells [Journal of Virology, 65, 4107–4113 (1991)].

Furthermore, using these viral reconstitution techniques, gene therapy vectors have been developed [Bio/Technology, 11, 916–920 (1993); Nucleic Acids Research, 23, 1495–1501 (1995); Human Gene Therapy, 6, 1161–1167 (1995); Methods in Cell Biology, 43, 43–53 (1994); Methods in Cell Biology, 43, 55–78 (1994)].

However, as described above, in spite of many advantages of Sendai virus to be industrially useful virus, its reconstitution system has not been established, because it is a negative-strand RNA. This is due to tremendous difficulty in reconstituting viral particles via viral cloned cDNAs.

As described above, it has been clearly demonstrated that a mere introduction of RNA from negative-strand RNA virus (vRNA) or its complementary strand RNA (cRNA) into host cells does not support the generation of negative-strand RNA virus. This is absolutely different from the case of positive strand RNA viruses. Although, in Tokkai H4-211377, "methods for preparing cDNAs corresponding to negative strand RNA viral genome and infectious negative strand RNA virus" are disclosed, the entire experiments of said documents described in "EMBO. J., 9, 379–384 (1990) were later found to be not reproducible, so that the authors themselves had to withdraw all the article contents [see EMBO J., 10, 3558 (1991)]. Therefore, it is obvious that techniques described in Tokkai H4-211377 do not correspond to the related art of the present invention.

Reconstitution systems of negative strand RNA viruses were reported for influenza virus [Annu. Rev. Microbiol., 47, 765–790 (1993); Curr. Opin. Genet . Dev., 2, 77–81 (1992)]. Influenza virus is a negative strand RNA virus having an eight-segmented genome. According to these literatures, a foreign gene was first inserted into the cDNA of one of said genome segments, and then RNA transcribed from the cDNA of all eight segments containing the foreign gene was assembled with the virus-derived NP protein to form RNP. Then, the virus reconstitution was achieved by providing host cells with these RNPs and an RNA-dependent RNA polymerase. Thereafter, the reconstitution of negative single-stranded RNA virus from cDNA was reported for rabies virus belonging to the rhabdovirus family [J. Virol., 68, 713–719 (1994)].

Therefore, although techniques for reconstituting negative strand viruses have become fundamentally known to the public, in the case of Sendai virus, the direct application of these techniques did not support the viral reconstitution. Also, the reconstitution of viral particles reported on the rhabdovirus was confirmed only by the expression of marker genes, RT-PCR, etc. Furthermore, the yield was not satisfactory for practical applications. Besides, in order to provide factors required for the viral reconstitution within host cells, helper viruses such as wild type viruses, recombinant vaccinia virus, etc. were conventionally introduced to host cells together with nucleic acids of the virus to be reconstituted. Accordingly, difficulties in separating the reconstituted desired virus from these harmful viruses were posing a difficult problem.

DISCLOSURE OF THE INVENTION

The purpose of the present invention is to establish an efficient system for reconstituting Sendai virus, enabling the gene manipulation of Sendai virus, and providing Sendai viral vector sufficiently useful in the field of gene therapy, etc.

In order to apply to the reconstitution test of Sendai virus, the present inventors first made various investigations using cDNAs derived from Sendai viral DI particles [ref. defective interfering particle in EMBO J., 10, 3079–3085 (1991)] or the minigenome of Sendai virus. As a result, they found efficient conditions regarding weight ratios among materials to be introduced into host cells, including cDNA, cDNAs concerning the transcription and replication, and the recombinant vaccinia virus to provide the T7RNA polymerase expression unit. Furthermore, the present inventors obtained full-length cDNAs of both positive and negative strands, constructed plasmids to induce the intracellular biosynthesis of positive or negative strand RNA of Sendai virus, and transferred said plasmid into host cells expressing cDNAs concerning the transcription and replication. As a result, they succeeded in re-constituting Sendai virus particles from cDNAs thereof. The present inventors also found for the first time that cDNAs introduced into host cells are more preferable in the circular form than in the linear form for the efficient reconstitution of viral particles, and that positive strand RNAs are superior to negative strand RNAs in the intracellular transcription for the highly successful reconstitution of viral particles.

In addition, the present inventors found that Sendai virus could be reconstituted even without using recombinant vaccinia virus as the T7RNA polymerase expression unit. That is, when the full-length RNA of Sendai virus transcribed in vitro was transferred into cells, and cDNAs encoding enzymes for the initial transcription and replication were transcribed under the control of T7 promoter, viral particles were reconstituted. This indicates that, if cells which express all enzymes required for the initial transcription and replication are constituted, the recombinant Sendai virus can be produced entirely without using helper viruses such as vaccinia virus. Since cells expressing all enzymes required for the initial transcription and replication were already described [J. Virology, 68, 8413–8417 (1994)], those skilled in the art will be able to form such cells with reference to said article. The cell described in said reference is the one derived from the 293 cell line carrying three out of Sendai viral genes, namely NP, P/C and L on its chromosome, and expressing proteins encoded by these three genes, NP, P/C and L.

From numerous examples of viral vectors, if viral particles can be efficiently reconstructed from nucleic acids, it is obvious that those skilled in the art are able to readily exchange desired viral gene, insert a foreign gene, or inactivate or delete a desired viral gene. That is, it will be obvious to those skilled in the art that the first success in reconstituting Sendai viral particles by the present invention has enabled the gene manipulation of Sendai virus.

That is, the present invention comprises the followings.
1. A recombinant Sendai virus having the genome with a desired foreign gene inserted or a desired gene deleted or inactivated, and retaining the disseminative capability.
2. The recombinant Sendai virus of description 1, wherein more than one gene encoding functional proteins are modified.
3. The recombinant Sendai virus of descriptions 1 or 2 comprising a foreign gene which can be expressed in host cells.
4. An RNA molecule comprising RNAs contained in the recombinant Sendai viruses of any one of descriptions 1–3.
5. An RNA molecule comprising cRNAs of RNAs contained in the recombinant Sendai viruses of any one of descriptions 1–3.
6. A kit consisting of the following two components.
   a. a DNA molecule comprising a template cDNA which can transcribe RNAs of descriptions 4 or 5, and
   b. a unit capable of transcribing RNAs of descriptions 4 or 5 with said DNA as template in vitro or intracellular.
7. A kit consisting of the following two components.
   a. a host expressing the NP, P/C and L proteins of Sendai virus (each protein may be replaced with a protein having an equivalent activity), and
   b. an RNA molecule of descriptions 4 or 5.
8. A method for producing the recombinant Sendai virus of descriptions 1–3, comprising introducing the RNA molecule of descriptions 4 or 5 into host cells expressing the NP, P/C and L proteins of Sendai virus (each protein may be replaced by a protein having the equivalent activity).
9. A kit consisting of the following three components,
   a. a host expressing the NP, P/C and L proteins of Sendai virus,
   b. a DNA molecule comprising a template cDNA capable of transcribing RNAs or cRNAs of descriptions 4 or 5, and
   c. a unit capable of transcribing RNAs of descriptions 4 or 5 with said DNA as template in vitro or intracellularly.

10. A method for producing the recombinant Sendai virus of descriptions 1–3, comprising introducing the DNA molecule comprising a template cDNA capable of transcribing RNAs of descriptions 4 or 5, and a unit capable of transcribing RNAs of descriptions 4 or 5 with said DNA as template in vitro or intracellularly into hosts expressing the NP, P/C and L proteins of Sendai virus.

11. A method for preparing foreign proteins comprising a process for infecting hosts with the recombinant Sendai virus of description 3, and recovering expressed foreign proteins.

12. A culture medium or chorio-allantoic fluid containing expressed foreign proteins obtainable by introducing the recombinant Sendai virus of description 3 into hosts and recovering said culture medium or chorio-allantoic fluid.

13. A DNA molecule realizing the expression of a protein encoded by a foreign gene integrated into a Sendai viral vector comprising said foreign gene inserted downstream of a promoter in an orientation for transcribing antisense RNA encoding said protein, and the said promoter.

Recombinant Sendai viral vectors of the present invention can be obtained, for example, by in vitro transcribing the recombinant cDNA encoding the gene-technologically produced recombinant Sendai viral vector genome, producing the recombinant Sendai viral genome RNA, and introducing said RNA to a host simultaneously expressing the NP, P/C and L proteins (each protein may be a protein with an equivalent activity) of Sendai virus. Alternatively, Sendai viral vectors of the present invention can be obtained by introducing a) the recombinant cDNA coding for the gene-technologically produced recombinant Sendai viral vector genome, and b) a unit capable of intracellularly transcribing RNA with said DNA as template into a host simultaneously expressing the NP, P/C and L proteins (each protein may be a protein having an equivalent activity) of Sendai virus. In this case, said recombinant cDNA a) may be inserted downstream of a specific promoter, and said transcription unit b) may be a DNA molecule expressing a DNA-dependent RNA polymerase acting on said specific promoter.

Sendai virus, the starting material in the present invention for the insertion of a desired foreign gene, or the deletion or inactivation of a desired gene may be a strain classified to parainfluenza virus type I, exemplified by Sendai virus Z strain or Fushimi strain. Furthermore, incomplete viruses such as DI particles, synthetic oligonucleotides, etc. may be used partial materials.

Also, so far as the recombinant Sendai virus of the present invention maintain the disseminative capability, any foreign gene may be inserted at any site of RNA comprised in said recombinant, and any genome gene may be deleted or modified. Foreign genes to be inserted may be exemplified by genes encoding various cytokines and peptide hormones which can be expressed within hosts. In order to express the desired protein, the foreign gene encoding said desired protein is inserted. In the Sendai viral RNA, it is preferable to insert a sequence of bases of 6 multiplication in number between the sequences R1 (5'-AGGGTCAAAGT-3') and R2 (5'-GTAAGAAAAA-3') [Journal of Virology, Vol. 67, No. 8 (1993) p.4822–4830]. Levels of expression of a foreign gene inserted into a vector can be regulated by virtue of the site of gene insertion and the base sequences flanking said foreign gene. For example, in the case of Sendai viral RNA, it is known that there are increasing levels of expression of the inserted gene with decreasing distance of said gene from the NP gene. Preferred hosts for expressing desired proteins may be any cells susceptible to the infection by the recombinant Sendai virus, exemplified by mammalian cells and chicken eggs. It is possible to efficiently produce the foreign gene product by infecting these hosts with the recombinant Sendai virus integrated with expressible foreign gene and recovering the expressed foreign gene product. For example, proteins thus expressed can be recovered by the standard method from the culture medium when cultured cells are the host, and chorio-allantoic fluid when chicken eggs are the host.

When a foreign gene is inserted into a plasmid for expressing the negative strand Sendai viral RNA, it is necessary to insert said foreign gene downstream of the promoter in an orientation for transcribing an antisense RNA of said foreign gene encoding a protein. Such "a DNA molecule for expressing a protein encoded by a foreign gene integrated into a Sendai viral vector comprising the foreign gene inserted downstream of the promoter in an antisense orientation for transcribing antisense RNA of said foreign gene encoding said protein and said promoter" has become available for the first time by the present invention, comprising a part of said invention.

Also, for example, in order to inactivate genes for immunogenicity, or enhance the efficiency of RNA transcription and replication, part of genes related with RNA replication of Sendai virus may be modified. Concretely, for example, at least one of the replication factors, the NP, P/C and L proteins may be modified to enhance or reduce the transcription and replication capabilities. The HN protein, one of the constitutional proteins, has dual activities as hemagglutinin and neuraminidase. For example, the reduction of the former activity may increase the viral stability in blood stream, and the modification of the latter activity may enable the regulation of viral infectivity. Also, the modification of the F protein mediating membrane fusion may be useful for improving membrane fusion liposomes constructed by fusing the reconstituted Sendai virus and artificial liposomes enclosing a desired drug or gene.

The present invention has enabled the introduction of point mutation and insertion at any sites of the genomic RNA, and is highly expected to accelerate the accumulation of genetic information on viral functions. For example, once the mechanism of viral RNA replication is elucidated, it may become possible to develop a viricide less harmful to a host cell and targeting nucleic acid replication process by utilizing the differences between the viral and host-cellular metabolisms of nucleic acid. In addition, the elucidation of functions of viral gene-encoded proteins may contribute to the development of viricides targeting proteins involved in infectivity and forming capability of viral particles. Concretely, for example, these techniques may be used for the analysis of antigen-presenting epitopes of the F and HN proteins which may act as antigenic molecules on the cell surface. Also, when a host cell gene for viral resistance is activated by viral infection, resulting in an elevated viral resistance, important information on such activation mechanism of host gene may be obtained by the genetic analysis of viral functions. Since Sendai virus is effective in inducing interferons, it is used in various basic studies. By analyzing the genome region necessary for inducing interferons, it may be possible to produce a non-viral interferon inducer. Techniques of the present invention are useful for the development of vaccines. Live vaccines may be produced by inoculating the recombinant Sendai virus with attenuating mutations to embryonated chicken eggs. Information thus obtained may be applied to other negative strand viruses, such as measles virus and mumps virus, with high demand for live vaccines. Furthermore, the present invention has enabled the usage of the recombinant Sendai virus as vectors for gene therapy. Since virus vectors of the present invention derived from Sendai virus are highly safe in the clinical application-and disseminative, and expected to be therapeutically effective with a relatively small dosage. In addition, when the suppression of a viral vector replication becomes necessary at the completion of therapy or during the therapy, only the viral vector replication can be specifically suppressed without damaging hosts by administering an inhibitor of RNA-dependent RNA polymerase.

BEST MODE FOR CARRYING OUT THE INVENTION

In the following, the present invention will be concretely described with reference to examples, but is not limited to these examples.

[EXAMPLE 1]

Figure 1:
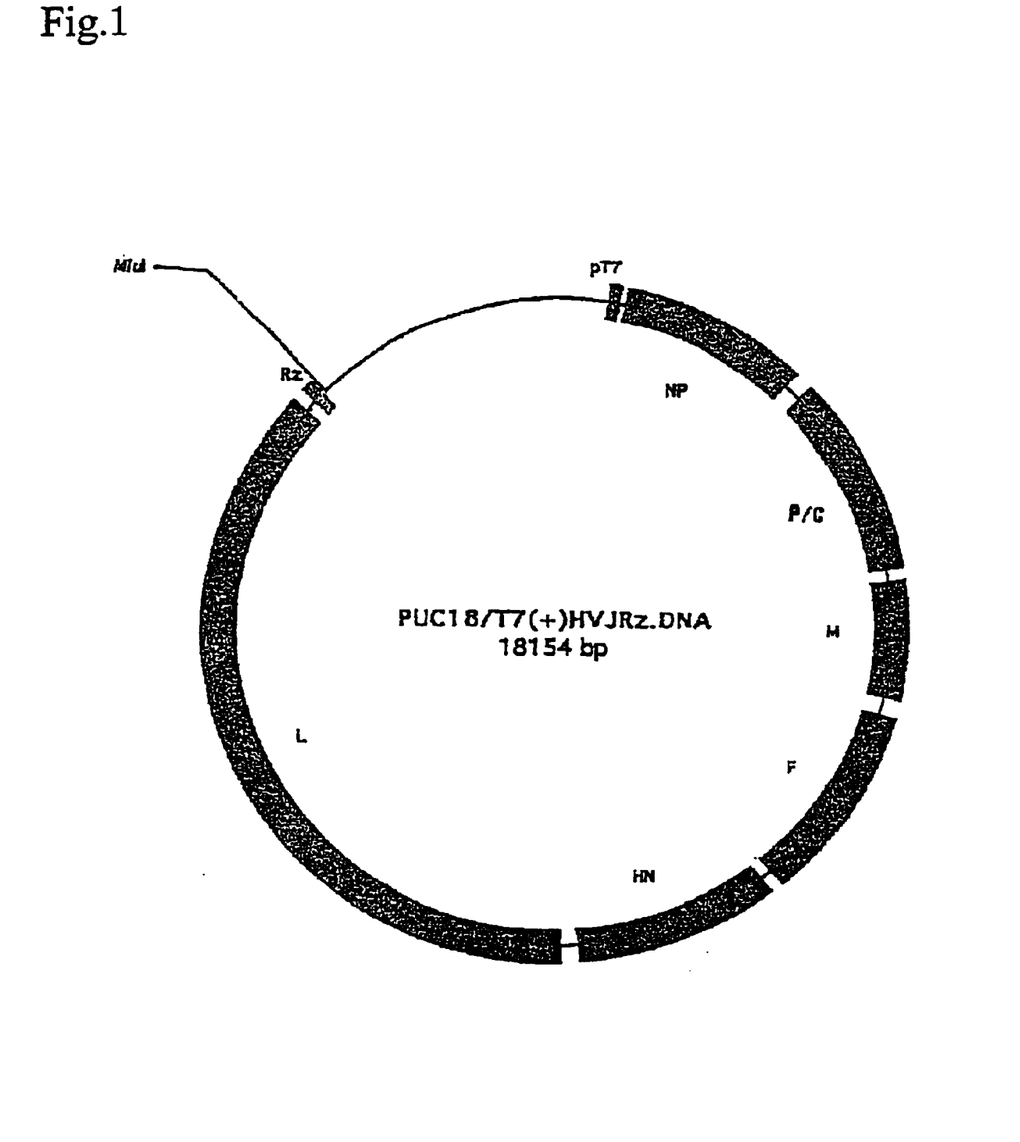
FIG. 1 is a schematic representation of plasmid pUC18/T7(−)HVJRz.DNA.
Figure 2:
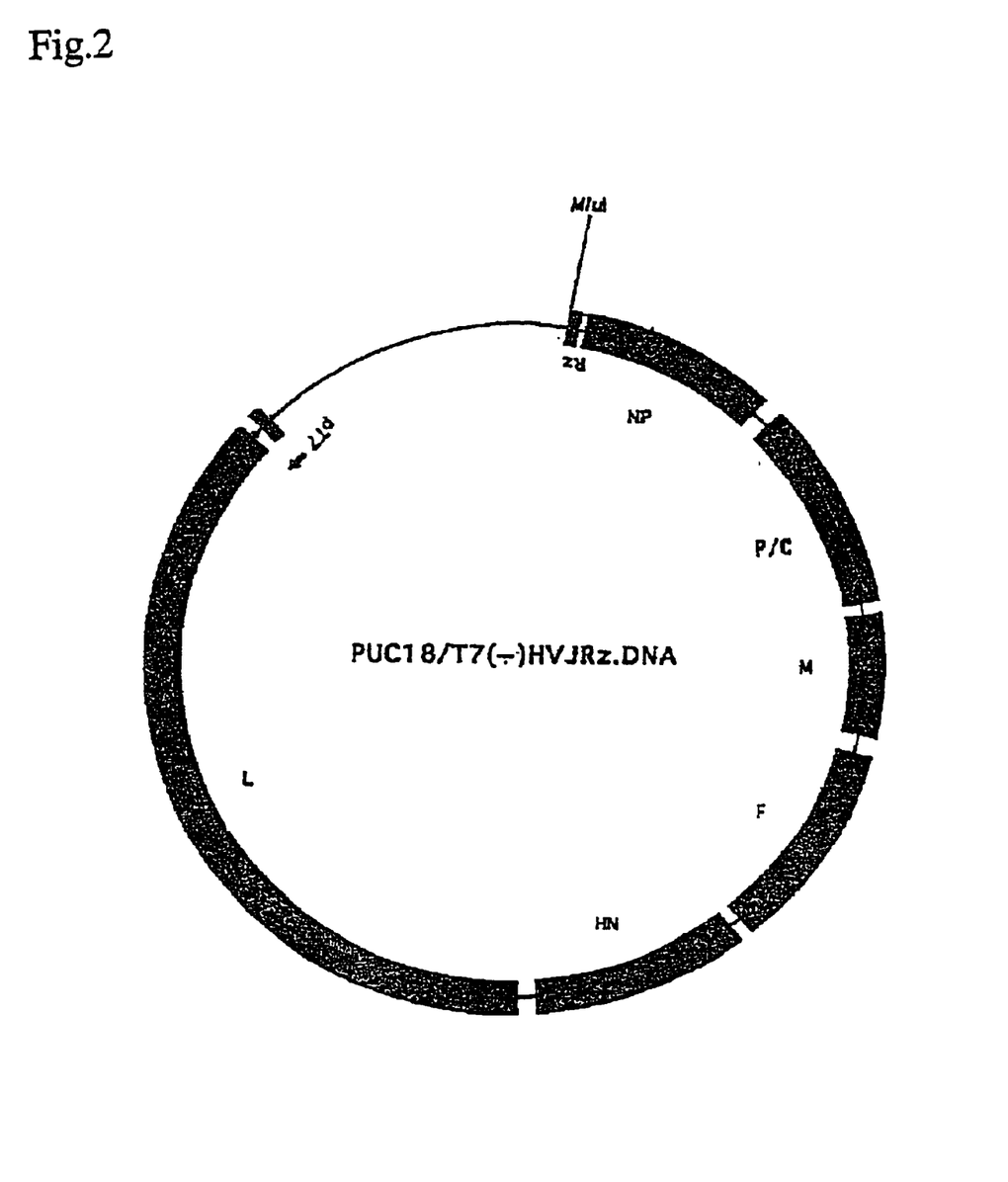
FIG. 2 is a schematic representation of plasmid pUC18/T7(−)HVJRz.DNA.

Preparation of Sendai virus transcription units pUC18/T7(−)HVJRz.DNA and pUC18/T7(+)HVJRz.DNA Plasmid pUC18/T7 (−)HVJRz.DNA was constructed by inserting a DNA molecule comprising T7 RNA polymerase promoter, Sendai virus cDNA designed to be transcribed to the negative strand RNA and the ribozyme gene in this order into PUC8 vector. Also, plasmid pUC18/T7 (+) HVJRz.DNA was constructed by inserting a DNA molecule comprising T7 RNA polymerase promoter, Sendai virus cDNA designed to be transcribed to the positive strand RNA and the ribozyme gene in this order into pUC18 vector. Constructions of pUC18/T7(−)HVJRz.DNA and pUC18/T7 (+)HVJRz.DNA are shown in FIGS. 1 and 2, respectively.

[EXAMPLE 2]

Reconstitution experiment of Sendai virus from cDNA

LLC-MK2 cells ($2\times10^6$) trypsinized in a usual manner were placed in a 60-mm diameter plastic dish, and incubated in MEM medium (MEM supplemented with 10% FBS) (2 ml) in a 5% $CO_2$ atmosphere at 37° C. for 24 h. After removing the medium and washing with PBS (1 ml), a suspension of recombinant vaccinia virus vTF7-3 expressing T7 polymerase in PBS (0.1 ml) was added to the cells at the multiplicity of infection (moi) of 2. The dish was gently agitated every 15 min to thoroughly spread the viral solution for 1 h infection. After removing the viral solution and washing with PBS (1 ml), a medium containing cDNA, which was prepared as follows, was added to the dish.

Nucleic acids shown in Tables 1 and 2 (containing plasmids expressing factors required for the replication of Sendai virus, pGEM-L, pGEM-P/C and pGEM-NP) were placed in a 1.5-ml sampling tube, and adjusted to a total volume of 0.1 ml with HBS (Hepes buffered saline; 20 mM Hepes pH 7.4 containing 150 mM NaCl) . In those tables, (−) and (+)cDNAs represent plasmids pUC18/T7(−)HVJRz.DNA and pUC8/T7 (+)HVJRZ.DNA, respectively, and /C and /L indicate that cDNA is introduced into cells in the circular form and linear form after the treatment with restriction enzyme M1uI, respectively.

On the other hand, in a polystyrene tube were placed HBS (0.07 ml), DOTAP (Boehringer Mannheim) (0.03 ml). To this tube was added the nucleic acid solution described above, and the mixture was left standing as such for 10 min. Then, to this mixture was added the cell culture medium described above (2 ml, MEM supplemented with 10% FBS) followed by the vaccinia virus inhibitors, rifampicin and cytosine arabinoside C (C/Ara/C), to the final concentrations of 0.1 mg/ml and 0.04 mg/ml, respectively, resulting in the preparation of the medium containing cDNA described above.

The dish described above was incubated in a 5% $CO_2$ atmosphere at 37° C. for 40 h. The cells in the dish were harvested using a rubber policeman, transferred to an Eppendorf tube, sedimented by centrifuging at 6,000 rpm for 5 min, and re-suspended in PBS (1 ml). Aliquots of this cell suspension, as such or after diluted, were inoculated to 10-days old developing embryonated chicken eggs. That is, the cell suspension was diluted with PBS to the cell numbers shown in Table 1, and eggs inoculated with its 0.5-ml aliquots were incubated at 35° C. for 72 h, then at 40° C. overnight. Chorio-allantoic fluid was recovered as virus solution from these eggs using a syringe with a needle.

Hemagglutinin unit (HAU) and plaque forming unit (PFU) of the recovered virus solution were assayed as follows.

HAU was determined as follows. Chicken blood was centrifuged at 400× g for 10 min and the supernatant was discarded. Precipitates thus obtained were suspended in 100 volumes of PBS, and centrifuged at 400× g for 10 min to discard the supernatant. This procedure was repeated twice to prepare an 0.1% blood cell solution. Two-fold serial dilutions of virus solutions were prepared, and 0.05 ml each dilution to be assayed was dispensed into each well of 96-well titer plate. The blood cell solution (0.05 ml each) was further added to each well, gently swirled to ensure a thorough mixing, and left at 4° C. for 40 min. The highest virus dilution to cause the hemagglutination observable with the naked eye was taken as HAU.

PFU was assayed as follows. CV-1 cells were grown to a monolayer on a 6-well culture plate. After the culture medium was discarded, a virus solution 10-fold serially diluted (0.1 ml each) was dispensed into each well of the culture plate to infect the cells at 37° C. for 1 h. During the infection, a mixture of 2× MEM free of serum and melted 2% agar (55° C.) was prepared, and trypsin was added to the mixture to a final concentration of 0.0075 mg/ml. After 1 h infection and removal of the virus solution, the culture medium mixed with agar (3 ml each) was added to each well of the culture plate, and incubated under a 5% $CO_2$ atmosphere at 37° C. for 3 days. Phenol red (0.1%) (0.2 ml) was added to each well, incubated at 37° C. for 3 h, and then removed. Unstained plaques were counted to estimate the virus titer as PFU/ml.

Table 1 shows Sendai virus template cDNAs transfected into LLC-2 cells, amounts of cDNA factors, pGEM-L, pGEM-P/C, and pGEM-NP, required for the RNA replication, incubation time, cell numbers inoculated to chicken eggs, HAU and PFU values.

TABLE 1

| Template cDNA | Total amount (μg) | pGEM-L (μg) | pGEM-P/C (μg) | pGEM-NF (μg) | Incubation time (h) | Amount of cells | HAU | PFU |
|---|---|---|---|---|---|---|---|---|
| (+) cDNA/C | 10 | 4 | 2 | 4 | 40 | $1.00 \times 10^5$ | 512 | $2 \times 10^9$ |
| (+) cDNA/C | 10 | 4 | 2 | 4 | 40 | $1.00 \times 10^5$ | 256 | $9 \times 10^8$ |
| (+) cDNA/C | 10 | 4 | 2 | 4 | 40 | $1.00 \times 10^6$ | 256 | $9 \times 10^8$ |
| (+) cDNA/L | 10 | 4 | 2 | 4 | 40 | $1.00 \times 10^5$ | <2 | <10 |
| (+) cDNA/L | 10 | 4 | 2 | 4 | 40 | $1.00 \times 10^5$ | <2 | <10 |
| (+) cDNA/L | 10 | 4 | 2 | 4 | 40 | $1.00 \times 10^6$ | <2 | <10 |
| (−) cDNA/L | 10 | 4 | 2 | 4 | 40 | $1.00 \times 10^4$ | <2 | <10 |
| (−) cDNA/L | 10 | 4 | 2 | 4 | 40 | $1.00 \times 10^5$ | <2 | <10 |
| (−) cDNA/L | 10 | 4 | 2 | 4 | 40 | $1.00 \times 10^6$ | <2 | <10 |
| (−) cDNA/C | 10 | 4 | 2 | 4 | 40 | $1.00 \times 10^4$ | <2 | <10 |
| (−) cDNA/C | 10 | 4 | 2 | 4 | 40 | $1.00 \times 10^5$ | <2 | <10 |
| (−) cDNA/C | 10 | 4 | 2 | 4 | 40 | $1.00 \times 10^6$ | 4 | $8 \times 10^3$ |

Samples showing both HAU and PFU were sedimented by ultra-centrifugation, re-suspended, purified by a sucrose density gradient centrifugation from 20% to 60%, and fractionated by 12.5% SDS-PAGE. Each protein contained in these samples was the same in size as that of Sendai virus.

These results demonstrated that Sendai virus can be reconstituted by introducing cDNAs into cells, and that virus particles are more efficiently reconstituted by introducing cDNAs transcribing positive strand RNAs as compared with those transcribing negative strand RNAs, and further by introducing cDNAs in the circular form rather in the linear form.

[EXAMPLE 3]

Survey of RNA replication factors required for Sendai virus reconstitution

Experiments were performed to examine whether all three plasmids expressing the L, P/C and NP proteins were required for the reconstitution of Sendai virus. Experimental methods were similar to those described in Example 2 except that any combinations of two out of pGEM-L, pGEM-P/C and pGEM-NP plasmids or only one out of them, instead of all these three combined as in Example 2, were introduced together with a template cDNA into cells.

Table 2 shows Sendai virus template cDNAs introduced into LLC-MK2 cells, amounts of the cDNA factors required for RNA replication including pGEM-L, pGEM-P/C and pGEM-NP, incubation time, number of cells inoculated into chicken eggs, and values of HAU and PFU.

TABLE 2

| Template cDNA | Total amount (μg) | pGEM-L | pGEM-P/C | pGEM-NF | Incubation time (h) | Number of cells inoculated | HAU | PFU |
|---|---|---|---|---|---|---|---|---|
| (+) cDNA/C | 10 | 4 | 2 | 4 | 40 | $1.00 \times 10^5$ | 256 | $6 \times 10^8$ |
| (+) cDNA/C | 10 | 4 | 2 | 4 | 40 | $1.00 \times 10^6$ | 512 | $4 \times 10^9$ |
| (+) cDNA/C | 10 | 0 | 2 | 4 | 40 | $1.00 \times 10^6$ | <2 | <10 |
| (+) cDNA/C | 10 | 0 | 2 | 4 | 40 | $1.00 \times 10^6$ | <2 | <10 |
| (+) cDNA/C | 10 | 4 | 0 | 4 | 40 | $1.00 \times 10^6$ | <2 | <10 |
| (+) cDNA/C | 10 | 4 | 0 | 4 | 40 | $1.00 \times 10^6$ | <2 | <10 |
| (+) cDNA/C | 10 | 4 | 2 | 0 | 40 | $1.00 \times 10^6$ | <2 | <10 |
| (+) cDNA/C | 10 | 4 | 2 | 0 | 40 | $1.00 \times 10^6$ | <2 | <10 |
| (+) cDNA/C | 10 | 0 | 0 | 4 | 40 | $1.00 \times 10^6$ | <2 | <10 |
| (+) cDNA | 10 | 0 | 0 | 4 | 40 | $1.00 \times 10^6$ | <2 | <10 |
| (+) cDNA/C | 10 | 0 | 2 | 0 | 40 | $1.00 \times 10^6$ | <2 | <10 |
| (+) cDNA/c | 10 | 0 | 2 | 0 | 40 | $1.00 \times 10^6$ | <2 | <10 |
| (+) cDNA/C | 10 | 4 | 0 | 0 | 40 | $1.00 \times 10^6$ | <2 | <10 |
| (+) cDNA/C | 10 | 4 | 0 | 0 | 40 | $1.00 \times 10^6$ | <2 | <10 |

As shown in Table 2, no virus reconstitution was observed by introducing any combinations of two out of these three factors into cells, confirming the necessity of all three proteins L, P/C and NP for the virus reconstitution.

[EXAMPLE 4]

Reconstitution experiment of Sendai virus in vitro from transcribed RNAs

Since the reconstitution of Sendai virus from the functional cDNA clones was described in Example 2, it was further examined whether transcription products of said cDNAs in vitro, that is, vRNA and cRNA, can support similar reconstitution.

After the Sendai virus transcription units, pUC18/T7(−)HVJRz.DNA and pUC8/T7(+)HVJRz.DNA, were linearized with restriction enzyme MluI, using these DNAs as templates, RNA synthesis was performed in vitro with a purified T7 polymerase preparation (EPICENTRE TECHNOLOGIES: Ampliscribe T7 Transcription Kit). The method for synthesizing in vitro RNAs essentially followed the protocols provided with the kit. Using RNA products thus obtained in place of cDNAs in Example 2, similar experiments were performed, and the virus production was estimated by HA test. Results are shown in Table 3.

TABLE 3

| Template cDNA | Total amount (μg) | pGEM-L (μg) | pGEM-P/C (μg) | pGEM-NP (μg) | Incubation time (h) | Number of cells inoculated | HAU | PFU |
|---|---|---|---|---|---|---|---|---|
| in vitro (−) RNA | 10 | 4 | 2 | 4 | 40 | $1.00 \times 10^6$ | 512 | $2 \times 10^9$ |
| in vitro (−) RNA | 10 | 4 | 2 | 4 | 40 | $1.00 \times 10^6$ | 512 | ND |
| in vitro (+) RNA | 10 | 4 | 2 | 4 | 40 | $1.00 \times 10^6$ | 2 | $5 \times 10^3$ |
| in vitro (+) RNA | 10 | 4 | 2 | 4 | 40 | $1.00 \times 10^6$ | <2 | ND |

These results indicate that virus can be reconstituted by introducing either negative or positive sense strand RNAs into cells

[EXAMPLE 5]

Expression of foreign genes inserted into Sendai viral vectors in host cells

1. Preparation of Sendai virus vector "pSeVgp120" inserted with a foreign gene (HIV-1 gp120)

Using a set of primers comprising primer a (5'-TGCGGCCGCCGTACGGTGGCAATGAGTGAAGGAG-AAGT-3') (SEQ ID NO: 1) and primer d (5'-TTGCGGCCGCGATGAACTTTCACCCTAAGTTT-TTTATTACTACGGCG-TACGTCATCTTT TT-TCTCTCTGC-3') (SEQ ID NO:2), the HIV-1 gp120 gene was amplified on "pN1432" by the standard PCR techniques. PCR products were subjected to TA cloning, digested with NotI, and then inserted into the NotI site of "pSeV18+". Then, E. coli cells were transformed with this recombinant plasmid. DNAs were extracted from each colony of E. coli by the "Miniprep" method, digested with DraIII, and then electrophoresed. Positive clones (designated "clone 9" hereafter) were selected by confirming to contain DNA fragments of the size expected from the insertion. After DNA fragments were confirmed to have the authentic nucleotide sequence, DNAs were purified by a cesium chloride density gradient centrifugation. pSeV18 inserted with the gp120 gene is designated "pSeVgp120" hereafter.

2. Reconstitution of Sendai virus containing SeVgp120 (SeVgp120) and analysis of gp120 expression Except for the further transfection of pSeVgp120 into LLCMK2 cells, in addition to pGEM-NP, pGEM-P/C and pGEM-L, chorio-allantoic fluid was recovered from embryonated chicken eggs and assayed for the viral HAU by exactly as described in Example 2. The recovered virus was also examined for the expression of gp120 by ELISA as follows.

Samples (100 μl each) were dispensed into each well of a 96-well plate which had been coated with monoclonal antibody against HIV-1, and incubated at 37° C. for 60 min. After washing with PBS, HRP-linked anti-HIV-1 antibody (100 μl each) was added to each well, and incubated at 37° C. for 60 min. After washing with PBS, tetramethylbenzidine was added to each well, and amounts of reaction product converted by the action of HRP under acidic conditions were determined by following the optical density at 450 nm to estimate the expression amount of gp120. Results are shown in the left-hand column in Table 4.

The virus solution thus obtained was inoculated to CV-1 cells, and similarly examined as follows. CV-1 cells were dispensed to a culture plate at $5 \times 10^5$ cells/plate, grown, and then the culture medium was discarded. After washing with PBS (−), the viral solution was added to the cells at the multiplicity of infection of 10, and incubated at room temperature for 1 h. After the virus solution was discarded, washed with PBS(−), a plain MEM medium (MEM medium supplemented with antibiotics AraC and Rif, and trypsin) was added to the cells, and incubated at 37° C. for 48 h. After the reaction, the medium was recovered and assayed for HAU (by a similar method as described in Example 2) and examined for the expression of gp120 (by ELISA) . Results are shown in the center column of Table 4. In addition, the supernatant of CV-1 cell culture medium was inoculated to embryonated chicken eggs again, and the virus solution thus obtained was assayed for HAU and also examined for the gp120 expression (by ELISA). Results are shown in the right hand column of Table 4.

TABLE 4

| (μg/ml) | | |
|---|---|---|
| Chorio-allantoic fluid (F1) gp120 (HAU) | CV-1 medium (F1) gp120 (HAU) | Chorio-allantoic fluid (F2) gp120 (HAU) |
| 0.10 (4) | 3.46 (128) | |
| 0.15 (32) | 1.81 (128) | 1.56, 1.21 (512, 512) |
| 0.05 (32) | 2.20 (128) | |

As shown in Table 4, markedly high concentrations of gp120 were detected in CV-1 cells in culture (center column of the Table), and also in the chorio-allantoic fluids from embryonated chicken eggs inoculated again with the virus (right-hand column of the Table). In the left-hand and center columns of the Table are shown the mean values of three clones.

Furthermore, the expression of gp120 was analyzed by Western blotting. After the culture medium of CV-1 cells infected with Sevgp120 was centrifuged at 20,000 rpm for 1 h to sediment virus, the supernatant was treated with either TCA (10%, v/v) for 15 min on ice or 70% ethanol at −20° C., and centrifuged at 15,000 rpm for 15 min. Proteins thus precipitated were mixed to react with an "SDS-PAGE sample buffer" (Daiichi Chemicals) at 90° C. for 3 min, and then subjected to electrophoresis on 10% SDS-polyacrylamide gel (SDS-PAGE). Proteins thus fractionated were transferred to PVDF membranes (Daiichi Chemicals), reacted with monoclonal antibody 902 at room temperature for 1 h, and then washed with T-TBS. The membranes were reacted with anti-mIgG (Amersham) at room temperature for 1 h, and washed with T-TBS. The membranes were then reacted with HRP-linked protein A (Amersham) at room temperature for 1 h, washed with T-TBS, and 4-chloro-1- naphthol (4CNPlus) (Daiichi Chemicals) was added to detect gp120. As a result, protein bands were visualized at positions corresponding to the expected molecular weight of gp120.

Figure 3:
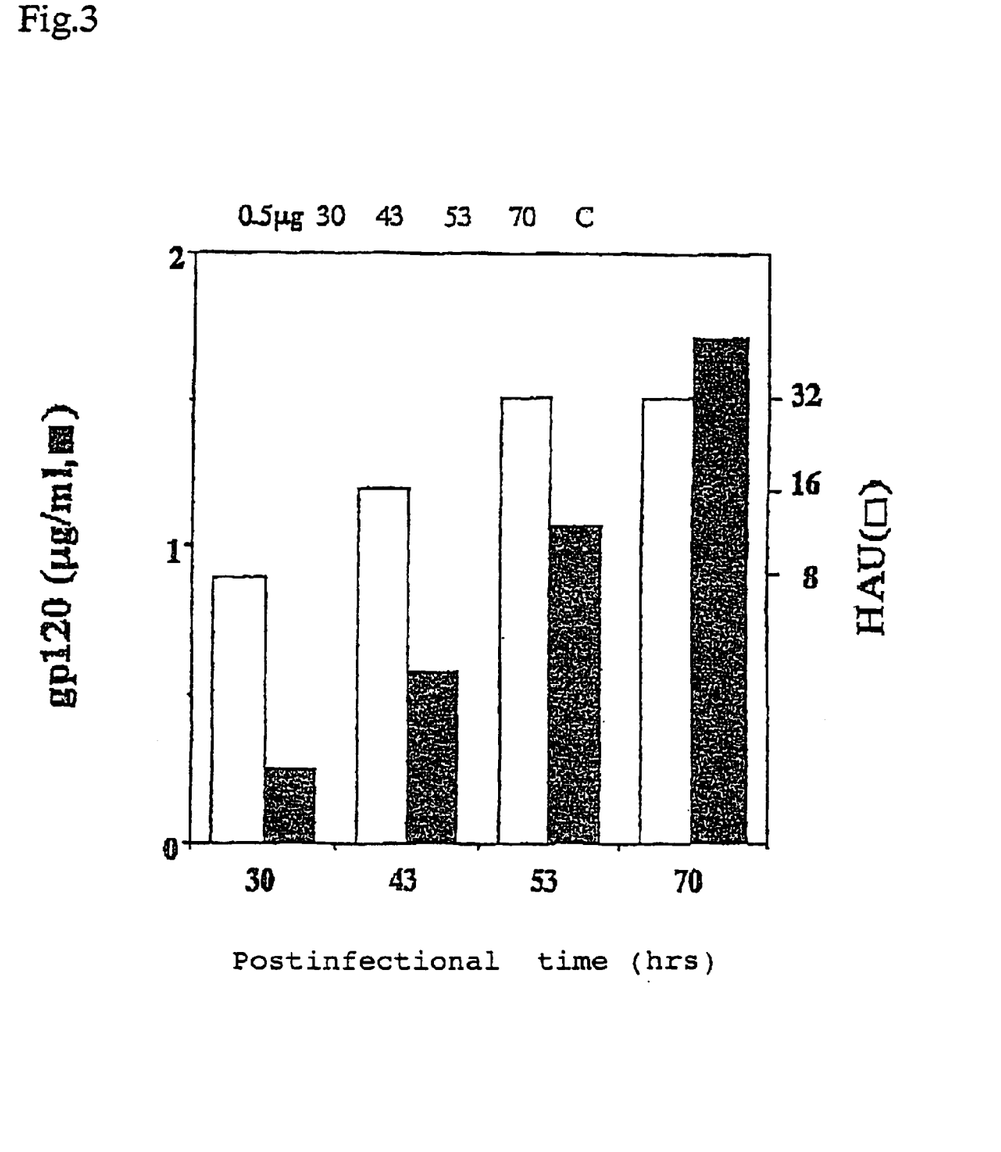
FIG. 3 is a graphic representation of the relationship between the postinfection time of CV-1 cells with SeVgp120 and HAU as well as the level of gp120 expression.

In addition, effects of postinfection time of CV-1 cells transfected with SeVgp120 on the HAU value and gp120 expression amount were analyzed. CV-1 cells ($5 \times 10^6$) dispensed to 10-cm plate were infected with SeVgp120 at the multiplicity of infection of 10, and the culture medium (1 ml each) was postinfectionally recovered at 30, 43, 53 and 70 h, mixed with an equal volume of the fresh medium, and subjected to HAU assay, gp120 expression examination (by ELISA) and Western blotting. Results are shown in FIG. 4. As clearly shown in FIG. 3, the production of gp120 tends to increase with the increasing HA titer of Sendai virus.

[EXAMPLE 6]

Analyses of SeVgp120 propagation and gp120 expression level in various types of cells Using similar methods as those in Example 5 except for the use of various types of cells, HAU and gp120 expression levels (by ELISA) were assayed. Results are shown in Table 5.

TABLE 5

| Cell type | Time (postinfection) | HAU | rgp120 (µg/ml) |
|---|---|---|---|
| CV-1 | 96 | 32 | 2.5 |
| LLCMK2 | 48 | 16 | 0.5 |
| CHO | 55 | 4 | 0.46 |
| NIH3T3 | 48 | 4 | 0.25 |
| MT4 | 24 | 16 | 0.8 |
| MOLT4/ | 24 | 16 | 1.2 |

In the left-hand column of the Table are shown the postinfectional times of various types of cells transfected with SeVgp120. As a result, SeVgp120 propagation and gp120 expression were detected in all types of cells tested.

[EXAMPLE 7]

Studies on the expression of luciferase gene inserted into the Sendai viral vector in host cells In order to isolate the luciferase gene for inserting to vectors, the luciferase gene bounded by the engineered NotI sites on both termini was constructed by the standard PCR using a set of primers [5'-AAGCGGCCGCCAAAGTTCACGATGGAAGAC-3'] (30mer) (SEQ ID NO: 3)] and [5'-TGCGGCCGCGATGAACTTTCACCC-TAAGTTTTT-CTTACTACGGATTATTACAATTTGGA CTTTCCGCCC-3'(69mer) (SEQ ID NO: 4) with "pHvluciRT4" as a template. The PCR product was cloned into the NotI window of pSeV18$^+$ to obtain Sendai virus vector to which the luciferase gene was inserted. Then, this recombinant vector was transfected into LLCMK2 cells, and inoculated into embryonated chicken eggs. Chorio-allantoic membranes of developing eggs were excised out, twice washed with cold PBS (−), and, after the addition of a lysis buffer (Picagene WAKO) (25 µl) and thorough mixing, centrifuged at 15,000 rpm for 2 min. To the supernatant (5 µl each) was added the substrate (IATRON) (50 µl), and the mixture was dispensed into each well of a 96-well plate. Fluorescent intensity was measured with a luminometer (Luminous CT-9000D, DIA-IATRON), and the enzyme activity was expressed as counts per second (CPS). As a result, an extremely high luciferase activity was detected with CV-1 cells at 24-h postinfection (Table 6). In these experiments, Sendai virus which did not carry the luciferase gene was used as control (represented by "SeV" in the table). Results obtained from two clones are shown in the table.

TABLE 6

| | Fluorescence intensity (counts/10 sec) | |
|---|---|---|
| | Chorio-allantoic membrane | CV-1 (24 h postinfection) |
| Luc/SeV | 669187 | |
| | 2891560 | 8707815 |
| SeV | 69 | 48 |
| | 23 | 49 |

INDUSTRIAL APPLICABILITY

By the present invention, a system for efficient reconstitution of viral particles from Sendai viral cDNAs has been established, enabling the gene manipulation of Sendai virus to produce the recombinant Sendai virus comprising a genome with a desired foreign gene inserted or a desired gene deleted or inactivated, but retaining the disseminative capability.

What is claimed is:

1. A recombinant Sendai viral vector containing a Sendai viral genome carrying a foreign gene, wherein said vector allows for the expression in a host cell of both Sendai viral genes contained within said Sendai viral genome and said foreign gene.

2. An RNA molecule comprising RNA contained in the recombinant Sendai viral vector of claim 1.

3. An RNA molecule comprising cRNAs of RNAs contained in the recombinant Sendai viral vector of claim 1.

4. A kit comprising:
   a. a DNA molecule containing a template cDNA capable of transcribing RNA of claim 2 or 3, and
   b. a unit capable of transcribing said RNA with said DNA as template in vitro or intracellularly.

5. A kit comprising:
   a. a cell expressing Sendai viral proteins NP, P, and L, and
   b. the RNA molecule of claim 2 or 3.

6. A method for producing the recombinant Sendai viral vector of claim 1, comprising transfecting RNA of claim 2 or 3 to a cell wherein the cell expresses Sendai viral proteins NP, P, and L.

7. A kit consisting of the following three components:
   a. a cell expressing Sendai viral proteins NP, P, and L;
   b. a DNA molecule containing a template cDNA capable of transcribing RNA or cRNA of claim 2 or 3; and
   c. a unit capable of transcribing said RNA with said DNA as template in vitro or intracellularly.

8. A method for producing the recombinant Sendai viral vector of claim 1, wherein said method comprises introducing into a cell expressing Sendai viral proteins NP, P, and L a DNA molecule containing a template cDNA capable of transcribing RNA of claim 2 or 3, and a unit capable of transcribing said RNA with said DNA as a template intracellularly.

9. A method for producing a foreign protein, comprising a process of infecting a host cell with the recombinant Sendai viral vector of claim 1 and recovering the expressed foreign proteins, wherein said host cell is a tissue culture cell.

10. A cell culture medium containing expressed foreign proteins and Sendai virus particles or parts thereof, obtainable by:
  a. initially transfecting the recombinant Sendai viral vector of claim 1 to a first host cell, wherein said foreign gene integrated therein encodes a foreign protein;
  b. allowing said recombinant Sendai viral vector to disseminate to other host cells in the cell culture medium following said initial transfection of said recombinant Sendai viral vector into said host cells;
  c. allowing said host cells to express said foreign protein; and
  d. recovering said culture medium.

11. A DNA molecule for expressing a protein encoded by a foreign DNA integrated into a Sendai viral vector DNA, said Sendai viral vector DNA comprising:
  a. a promoter;
  b. a cDNA encoding an RNA molecule corresponding to the Sendai viral genome of claim 1; and
  c. DNA encoding a foreign DNA, wherein said foreign DNA is integrated within said Sendai viral genome and the Sendai viral genome containing said foreign DNA is inserted downstream of said promoter in an orientation for transcribing an antisense RNA of both said Sendai viral genome and said foreign DNA.

12. The recombinant Sendai viral vector of claim 1, wherein at least one gene encoding Sendai viral protein selected from the group consisting of NP, P, and L proteins, is deleted or modified.

13. The method of claim 8, wherein said virus is produced entirely without the use of a helper virus.

14. The kit of claim 5, wherein said cell does not express heterologous DNA-dependent RNA polymerase.

15. The method of claim 6, wherein said cell does not express heterologous DNA-dependent RNA polymerase.

16. A recombinant Sendai viral vector containing a Sendai viral genome in which at least one gene encoding a Sendai viral protein selected from the group consisting of NP, P, and L proteins, is deleted or inactivated, wherein all other Sendai virus genes, other than genes encoding NP, P, and L proteins, are retained.

17. The recombinant Sendai viral vector of claim 1, wherein said foreign gene is inserted prior to the ORF of the NP gene.

* * * * *

SEQUENCE LISTING

<160> NUMBER OF SEQ ID NOS: 6

<210> SEQ ID NO 1
<211> LENGTH: 38
<212> TYPE: DNA
<213> ORGANISM: Human immunodeficiency virus

<400> SEQUENCE: 1
tgcggccgcc gtacggtggc aatgagtgaa ggagaagt                38

<210> SEQ ID NO 2
<211> LENGTH: 69
<212> TYPE: DNA
<213> ORGANISM: Human immunodeficiency virus

```
<220> FEATURE:
<221> NAME/KEY: variation
<222> LOCATION: (35)...(35)
<223> OTHER INFORMATION: v at 35 is a, c, or g, not t or u.

<400> SEQUENCE: 2
ttgcggccgc gatgaacttt caccctaagt ttttvttact acggcgtacg tcatcttttt    60
tctctctgc                                                            69

<210> SEQ ID NO 3
<211> LENGTH: 30
<212> TYPE: DNA
<213> ORGANISM: Artificial Sequence
<220> FEATURE:
<223> OTHER INFORMATION: Chemical synthesis

<400> SEQUENCE: 3
aagcggccgc caaagttcac gatggaagac                                     30

<210> SEQ ID NO 4
<211> LENGTH: 69
<212> TYPE: DNA
<213> ORGANISM: Artificial Sequence
<220> FEATURE:
<223> OTHER INFORMATION: Chemical synthesis

<400> SEQUENCE: 4
tgcggccgcc atgaactttc accctaagtt tttcttacta cggattatta caatttggac    60
tttccgccc                                                            69

<210> SEQ ID NO 5
<211> LENGTH: 11
<212> TYPE: DNA
<213> ORGANISM: Sendai virus

<400> SEQUENCE: 5
agggtcaaag t                                                         11

<210> SEQ ID NO 6
<211> LENGTH: 10
<212> TYPE: DNA
<213> ORGANISM: Sendai virus

<400> SEQUENCE: 6
gtaagaaaaa                                                           10
```